United States Patent [19]

Snowden, Jr. et al.

[11] 4,203,725

[45] May 20, 1980

[54] METHOD AND TEST KIT FOR THE ON-SITE DETERMINATION OF THE PRESENCE OF CONTAMINANT MATERIAL IN LUBRICATING OIL

[75] Inventors: James E. Snowden, Jr.; Esther A. Snowden, both of Houston, Tex.

[73] Assignee: Contamoil Corporation, Santa Monica, Calif.

[21] Appl. No.: 877,371

[22] Filed: Feb. 13, 1978

[51] Int. Cl.² .................. G01N 31/22; G01N 33/28
[52] U.S. Cl. .......................... 23/230 HC; 23/230 R; 422/61
[58] Field of Search ......... 23/230 HC, 230 R, 230 M, 23/259; 422/61

[56] References Cited

U.S. PATENT DOCUMENTS

| | | | |
|---|---|---|---|
| 270,489 | 1/1883 | Schubert | 23/230 HC |
| 2,770,530 | 11/1956 | Bergstrom et al. | 23/230 HC |
| 3,030,190 | 4/1962 | Seemann et al. | 23/230 HC |
| 3,528,775 | 9/1970 | O'Hara et al. | 23/230 HC |
| 3,574,550 | 4/1971 | Scott | 23/230 HC |
| 3,585,000 | 6/1971 | Bremanis | 23/230 HC |
| 3,653,838 | 4/1972 | Glass | 23/230 HC |
| 3,808,149 | 4/1974 | Ellis et al. | 23/230 HC |
| 3,811,837 | 5/1974 | Hoffman | 23/230 HC |
| 3,955,927 | 5/1976 | Zelaskowski et al. | 23/230 HC X |
| 4,082,511 | 4/1978 | Bedford | 23/230 HC |

OTHER PUBLICATIONS

ASTM Test, D-811-848 (Revised 1974), Chemical Analysis for Metals in New & Used Lubricating Oil.
ASTM D664-58-Neutralization Value (Acid and Base Numbers) of Petroleum Products.
Det. of Trace Amts. of Copper, Borchardt et al., Analyt. Chem. vol. 29, No. 3, 3/57, pp. 414–419.
Det. of Trace Fe, Ni, V in Petroleum Oils, Anal. Chem., vol. 21, No. 12, Dec. 1949, pp. 1543–1545.
Det. of Equiv. Acidity & Basicity of Fertilizers, Pierre et al., Anal. Chem., vol. 10, 12, pp. 72–76.
J.A.C.S., Cohen, Mixed Indicators, pp. 1851–1857, vol. 44, 7–1922.
Oxid.-Reduct. Indicators for Use with Dichromate. Anal. Chem., vol. 6, pp. 465–466.
Use of Wide-Range Indic. for Det. of pH, McCrumb, Anal. Chem., vol. 3, No. 3, 7-15-31, pp. 233–235.

Primary Examiner—Michael S. Marcus
Attorney, Agent, or Firm—Phillips, Moore, Weissenberger, Lempio & Majestic

[57] ABSTRACT

A method and kit for the on-site determination of the presence and concentration of contaminant materials in lubricating oils is provided. According to the method, chemical analysis of representative samples of the lubricating oil establishes the concentration of preselected metal contaminants that may be existing in the oil sample. Concentration of acidic and/or basic contaminants is also determinable as a function of the pH value of the oil sample. Repetitive analysis of oil samples, according to the method of the invention, provides information regarding the quality of the oil during its lifetime in machines and/or engines and provides a basis for determining when the oil should be replaced with oil containing little or no contaminant material.

The invention also provides a kit for use in carrying out the method.

12 Claims, 1 Drawing Figure

METHOD AND TEST KIT FOR THE ON-SITE DETERMINATION OF THE PRESENCE OF CONTAMINANT MATERIAL IN LUBRICATING OIL

BACKGROUND OF THE INVENTION

1. Field of the Invention

This invention relates to a method and kit for the on-site determination of the presence of contaminant materials in lubricating oils through chemical analysis of representative samples of the lubricating oil.

2. Description of the Prior Art

Oil used in lubricating machines or engines is subject to mechanical wear and environmental degradation including, but not limited to, temperature, pressure, and atmospheric conditions which result in distinct wear metal trends, chemical decomposition of the oil or degradation of the machines or engines themselves, all having the effect of causing a build-up of contaminant materials within the lubricating oil. This build-up requires that the lubricating oil be periodically monitored in order to determine the concentration of contaminant materials present within the oil since as the contaminant material concentration increases, the remaining usable lifetime of the oil decreases to the point where continued use of oil containing a high concentration of contaminants is detrimental to the proper operation of the machine or engine. Such contaminant concentration increase necessitates replacement of the oil with oil containing a low concentration of contaminant materials to avoid machine or engine damage. Conversely, changing the lubricating oil too early in its operational lifetime results in significant and unnecessary expenses.

Machines, engines, or compressors used to power oil drilling, petrochemical or transportation equipment, utilize many gallons of lubricating oil. It is standard practice of oil manufacturers to add to the oil active extreme pressure and/or anti-corrosive materials which tend to inhibit the formation and/or build-up of contaminant materials. As the machines, engines, or compressors are operated, the concentration of active extreme pressure and/or anti-corrosive additives is depleted to the point where they fail to perform their inhibitory function, thus resulting in discernible increases in the amount of contaminant material existing within the lubricating oil. Further, these additives may be organic and/or organo-metallic chemical compounds which, due to the operating environment and conditions of the machines, may degrade into acidic and/or basic components. Such acidic and/or basic materials may have detrimental effects on the internal components of the machines, thereby also necessitating oil replacement.

Characteristically, the lubricating oil used in drilling, petrochemical, or transportation machines or engines has an operational lifetime dependent upon the quality of the lubricating oil, method of operation of the machines or engines, possible process contamination inherent in petrochemical production, and the environment parameters to which the lubricating oil is subjected. Failure to replace lubricating oil that contains a high concentration of contaminant material causes damage to the machines or engines themselves and results in very significant repair and replacement costs. Methods existing prior to the invention described herein for determining the concentration of contaminant materials in lubricating oils as generally described in chemical texts and ASTM manuals have utilized chemical procedures performed by a chemist or highly skilled technician at a laboratory site, all at a great cost of time and money. For example, it is a recognized practice to analyze lubricating oil with chemical instrumentation such as, for example an emission spectrometer sold by Baird-Atomic, Bedford, Mass. 01730 under the designation Model FAS-2 Fluid Analysis Spectrometer. Such analysis utilizes techniques analogous to emission spectrometry with the sample so analyzed being small quantities of lubricating oil in which is suspended minute particles of metals, i.e. wear metals. However, analysis of such oil by these techniques is difficult since the particle size of the wear metals directly influences the results obtained. For that reason emission spectrometry analysis techniques are considered semi-quantitative.

The current methods of analyzing such oil require that samples of the oil be sent to laboratories relatively far removed from the operational site. Since machines or engines are, in numerous industrial operations, used continuously it is essential that information regarding the quality of the lubricating oil be transmitted to the industrial site as quickly as possible to avoid the possibility that the lubricating oil then in use within the machines has exceeded its useful lifetime. As often is the case, current laboratory analysis of the lubricating oil at a place relatively far removed from the industrial site requires valuable time often in excess of the critical periods at which damage to the machines can occur. This extended period is due to the time involved in withdrawing a sample of the used oil, sending it to a laboratory, analyzing the sample, and transmitting the results back to the industrial site. Because of this time delay, the standard practice in industries such as the well drilling, petrochemical, and transportation industries is to replace the lubricating oil after an established operational lifetime dependent upon the operational and environmental parameters existing at the industrial site and, in some instances, without regard to the concentration of contaminants within the oil. A drawback of this standard practice is that very often the oil is replaced before the aforementioned contaminant material concentration is sufficiently high to warrant such replacement and contributes an unjustifiable expense to the cost of the entire industrial operation.

BRIEF DESCRIPTION OF THE DRAWING

The drawing briefly illustrates a kit in accordance with present invention.

SUMMARY OF THE INVENTION

Figure 1:
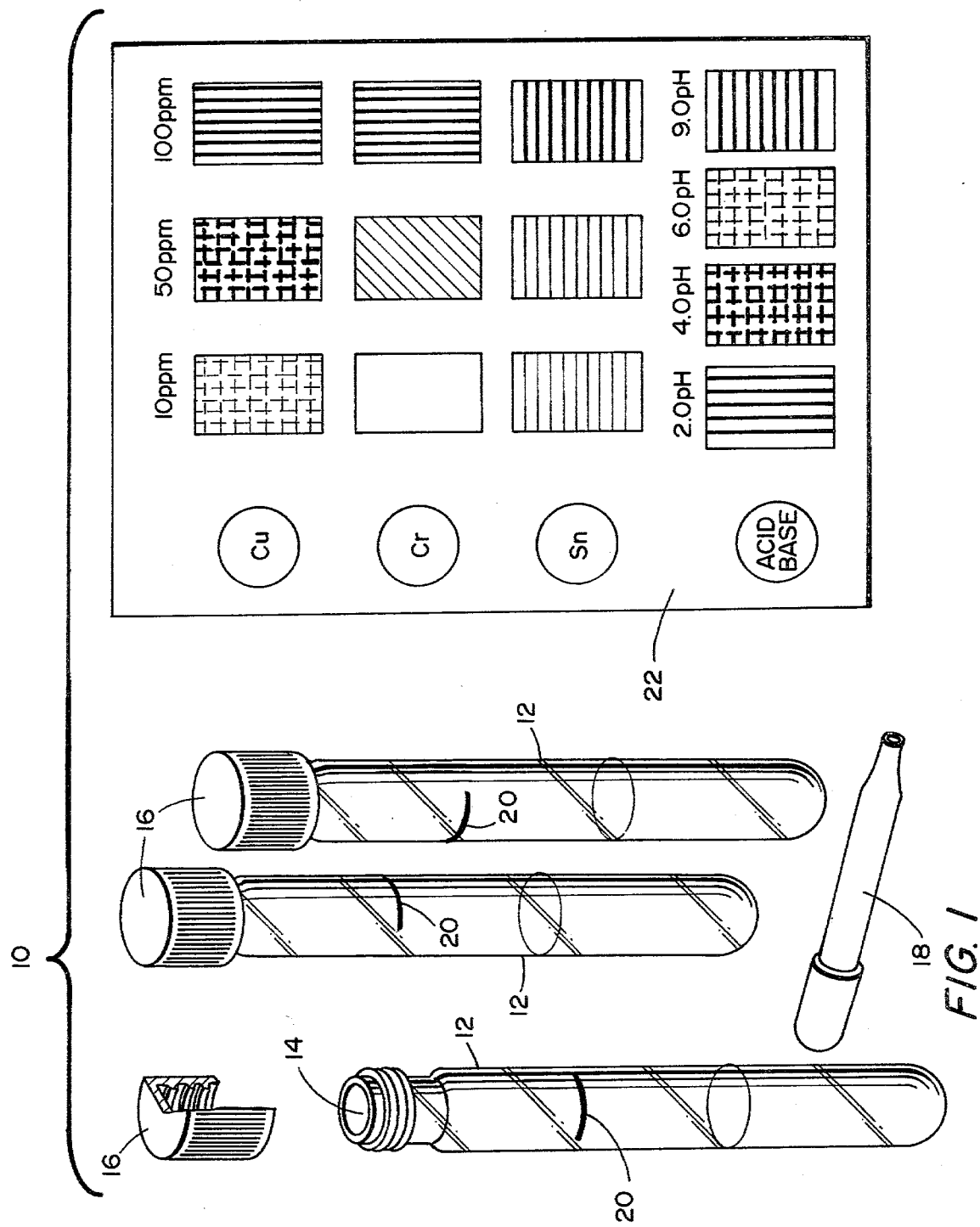

The present invention overcomes the above-noted and other shortcomings by providing a reliable, simple and inexpensive method and kit for the on-site determination of the presence of contaminant materials in lubricating oil. As used herein, the phrase "contaminant material" is meant to include inorganic, organic, and corrosive material.

A further feature of this invention is to provide a method for the on-site determination of the presence of contaminant materials in lubricating oil whereby a sample of freshly removed oil is mixed with a solvent of selected composition containing appropriate colorimetric agents of predetermined concentration, with the resulting mixture displaying color intensities due to the concentration of contaminants in the freshly removed oil. The color intensities vary depending upon this concentration. A comparison of the color intensities so obtained from freshly removed oil with standard color intensity values achieved by practicing the present invention on commercially available organo-metallic standards is indicative of the quality of the lubricating oil and further indicative of the quantity of contaminant materials existing within such oil.

The present invention also provides a method for the onsite determination of the concentration of contaminant materials and active anti-corrosive additives in lubricating oil. The presence of contaminant material is easily determined by mixing a representative sample of freshly removed oil with a known volume of solvent-reagent solution of selected composition and concentration to generate a color intensity indicative of the concentration of the contaminant material existing within the oil. Thereafter this resultant color intensity is compared to a color intensity obtained by mixing a sample of unused oil with a known volume of the same reactant solution of the same selected composition and concentration. Such comparison permits the generation of a signal indicative of the quantity of contaminant material existing within the lubricating oil.

Further, by practicing the method of this invention, as described above with respect to contaminant material on a representative sample of freshly removed oil, it is possible to establish the pH of the representative sample of freshly removed oil with the pH value indicative of the presence and concentration of acidic and/or basic corrosive materials within the oil and further indicative of the concentration of active anticorrosive additive in the oil.

The present invention also provides a lubricating oil analysis kit, with the components of the kit being preselected to permit analysis for one or more contaminant materials. The kit contains at least one receptacle for containing a preselected solvent-reagent solution of predetermined concentration with this solution adapted for the analysis of a preselected contaminant. The kit also includes a dispensing device for adding a volume of oil to the receptacle. Also included is a color chart displaying an accurate reproduction of selected color intensities indicative of the concentration of the preselected contaminant.

DESCRIPTION OF THE PREFERRED EMBODIMENT

The present invention embodies a method whereby the freshly removed representative oil sample is mixed with a solvent of selected composition and predetermined reagent concentration until a color intensity due to the contaminant concentration or pH value is achieved. This color intensity is manifest in a partitioned layer of the mixture which may be, for example, the lower phase of a two phase liquid system. Most importantly, the present invention permits the above-described analysis to proceed in an aqueous medium and eliminates the need of performing the separate step of extracting the contaminants from the oil base before analysis. Prior to the invention disclosed herein, it has been necessary to extract the contaminants from the oil by either reacting or complexing the contaminants with appropriate chemicals, removing the so extracted contaminants from the liquid system and thereafter performing analysis for the contaminant concentration. The present invention obviates the extraction by providing a suitable solvent and/or solvent-reagent solution with an aqueous base that effectively isolates the contaminant from the oil and permits an accurate determination of various color wavelengths and intensities in the aqueous layer with minimal interference from the generally opaque oil layer.

As used herein, the expression, "freshly removed representative oil" refers to oil that has been removed from a running engine or machine for a short period of time such that a determination of the presence of contaminant material and/or active anti-corrosive additives therein is approximately indicative of concentrations and/or amounts of contaminant material and active anti-corrosive additives in the same oil remaining in the running engine or machine.

As further used herein, "active anti-corrosive additive" is meant to include material added to the lubricating oil by the manufacturer which is capable of stabilizing the oil against the harmful increases of acidic and/or basic corrosive materials occurring during the operation of machines or engines in which the oil is placed.

As also used herein, the phrase, "used oil" refers to oil which is in place in an operating machine or engine and from which the freshly removed representative oil is withdrawn. The phrase "unused lubricating oil" refers to oil that has not been placed in an operational machine or engine. It is preferred that the unused lubricating oil be eventually placed in the machine or engine in order to further standardize the analysis procedure.

The reagents used in the practice of the present invention may be selected from a broad class of chemical compounds exhibiting oxidation-reduction, complexing, and/or acidic or basic properties. When analyzing for contaminants, the following reagents may be used: 1,10-phenanthroline, zinc dithiol, chromotropic acid, phosphoric acid, sodium hydroxide, bathocuproine disulphonic acid disodium salt, $\alpha,\alpha'$ dipyridyl, acetic acid, diphenyl carbazide, hydroxylamine hydrochloride, thioglycollic acid, and phosphomolybdic acid.

When analyzing for corrosive material or active anti-corrosive additive, indicators such as thymol blue, methyl orange, methyl green, alizarin, benzopurpurin, 4-$\beta$ metacresol purple, and congo red-curcumin are useful.

The solvents useful in the practice of the present invention may be a combination of chemicals having the ability to complex any contaminant material and/or active anti-corrosive additive existing in the freshly removed oil. As example, the solvent may be a combination of water, isopropyl alcohol; water, phosphoric acid; or water, sodium hydroxide, each in a ratio approximating 0.5 N:1 N.

ANALYSIS FOR INORGANIC CONTAMINANTS

The inorganic materials capable of being analyzed through the practice of the present invention would include those inorganic materials whose presence is made known by the operation of the machine itself. That is, the inorganic materials may be termed "wear metals" and would include those metals from which the machine is constructed such as, without limitation, iron, lead, copper, chromium, aluminum, nickel, silver, tin, silicon, boron, sodium, phosphorus, zinc, calcium, barium, magnesium, titanium, molybdenum, cadmium, vanadium and antimony. In the present invention, phosphorus is deemed to be a metal since it is often alloyed with one or more other metals for use in constructing machine components.

In the present invention, the inorganic contaminants may be metal particles (the size of which usually varies from generally equal to or greater than about 0.01 microns) or the oxides of such metals. Generally, when metal oxides are present they exist as surface layers on the particle surfaces. In this regard, the solvents of the present invention act to remove the inorganic contaminants from the oil by dissolving the metal oxides with the reagents thereafter reacting with or complexing the dissolved metal ions to form compounds exhibiting specific color characteristics. Further, the solvents and reagents of the present invention may be pre-mixed as a solvent-reagent solution of predetermined solvent and reagent concentration.

In order to establish reference points for the analysis of inorganic contaminants in freshly removed oil, organo-metallic standards may be used to provide concentration values selected as low, intermediate, and high values, such as for example 10, 50 and 100 parts per million, for the specific metal contaminants present in the lubricating oil. For example, the organo-metallic standards may be standards commercially available from the Conostan Division of Continental Oil Co., Ponca City, Okla. and sold under the trademark Conostan. Such materials as these are generally regarded as appropriate standards for use in oil analyses.

The method of the present invention in analyzing for inorganic contaminants proceeds as follows: A measured volume of a sample of freshly removed oil is placed in an appropriate receptacle such as, for example, a test tube capable of being tightly capped. A measured amount of solvent-reagent solution is added to the tube and thereafter, the sample tube is capped and shaken thoroughly. After shaking, the sample tube is placed in a vertical position to permit the freshly removed representative oil sample to separate from the solvent-reagent. The solvent-reagent phase, which may be found as the bottom layer of a 2-phase liquid, exhibits a color intensity indicative of the contaminant material existing within the used oil. Comparison of this color intensity with color intensity values obtained from practicing the method of the present invention on standard organo-metallic samples provides information indicative of the concentration of the contaminant material existing within the used oil. For example, the representative comparison value for metallic contaminants may be obtained in parts per million.

The method of making the above-referenced comparisons is not critical to the present invention. Accordingly, such comparisons may be made by standard spectrophotometric methods or by visually comparing the color intensity of the reacted oil sample with the color intensity generated by practicing the present invention on the organo-metallic standards. Further, the comparison may also be made by visually comparing the oil-generated color intensity to a color chart which reproduces the color intensities generated by the organo-metallic standards.

By testing samples of freshly removed oil at different times, one is thus able to derive data indicative of any increase in concentration of contaminant materials existing within the used oil.

In order to further standardize the obtained analytical results, it is preferred that the method disclosed herein be first performed on an unused lubricating oil of the same type and grade that is subsequently to be placed in an operating machine or engine. The color intensity which is obtained from such unused lubricating oil testing may be compared to the standard organo-metallic color intensities in order to derive the approximate concentration of contaminant materials existing within the unused lubricating oil. It is also preferred that one or more analyses be performed on freshly removed oil after the lubricating oil has been placed within the operating environment of the machine or engine.

Whenever the subsequent analysis establishes that the contaminant level has exceeded a predetermined value, for example 100 parts per million, for a specific metal contaminant, the lubricating oil contains a sufficiently harmful concentration of contaminants to warrant replacement.

As a further example, but without limitation, the method disclosed herein may be performed as follows:

Step 1. Place 4.5 ml of the selected solvent-reagent into a sample test tube capable of being capped;

Step 2. Place 4.5 ml of freshly removed oil in the sample test tube used in step 1, and cap the tube;

Step 3. Shake the mixture resulting from step 2 thoroughly for approximately 15 seconds until the solution is well mixed;

Step 4. Place the tube in a vertical position and allow to remain unattended for approximately 5 minutes or until the sample and solvent layers achieve separate phases;

Step 5. Compare the color intensity in the lower layer of the liquid phase to the color intensity of the same phase obtained by performing steps 1 through 4 on an organo-metallic standard to obtain a comparison value indicative of the concentration in parts per million of the contaminant material existing within the lubricating oil. Alternatively, the color intensity in the lower layer may be compared to a color chart which accurately reproduces the color intensities generated by the organo-metallic standards.

Table 1 provides examples of representative solvent-reagent combinations for the analysis of selected metal contaminants.

TABLE 1.

| CONTAMINANT | SOLVENT | REAGENT |
|---|---|---|
| Iron | Hydroxylamine HCl; water | α, α'dipyridil |
| Copper | Hydroxylamine HCl; water | Bathocuproine disulfonic acid disodium salt |
| Chromium | 85% Phosphoric acid water | Chromotropic acid disodium salt |
| Tin | water | Ammonium Molybdate |
| Nickel | water | Dimethylglyoxime disodium salt; ammonium tartarate |

Representative solvent and reagent systems for selected inorganic contaminant materials As noted from Table 1, analysis for nickel contaminant utilizes a dual reagent system with the water solvent dissolving any metallic oxides present in the oil. In the event oxides other than nickel are present such as, for example, iron, these oxides complex with the ammonium tartrate reagent to form an essentially colorless complex. Accordingly, any nickel present complexes with the disodium salt of dimethylglyoxime to form a colored complex. The color intensity of this complex is measured to determine the concentration of nickel existing within the lubricating oil sample.

DETERMINATION OF THE CONCENTRATIONS OF ACTIVE ANTI-CORROSIVE ADDITIVES

As previously mentioned, oil manufacturers often add active anti-corrosive additives to the oil produced. These additives are useful in stabilizing the oil against the harmful effects created by increases in acidic and/or basic decomposition products which may be formed in the oil during operation of the machines or engines. In this regard, the anti-corrosive additives may be considered as buffers. However, as the acidic and/or basic decomposition products increase in concentration the buffering effect of the additives concomitantly decreases to a point where slight increase in the concentration of the acidic and/or basic products produces a rapid and extreme change in the pH of the lubricating oil. Accordingly, the acidic or basic environment produced by this change warrants replacement of the oil with unused lubricating oil.

The method of the present invention of determining the presence and concentration of active anti-corrosive additives proceeds as follows: A measured volume of a sample of freshly removed oil is placed in an appropriate receptacle such as, for example, a test tube capable of being tightly capped. A measured amount of solvent-reagent solution is added to the tube and thereafter, the sample tube is capped and shaken thoroughly. After shaking, the sample tube is placed in a vertical position to permit the freshly removed representative oil sample to separate from the solvent-reagent. The solvent-reagent phase, which may be found as the bottom layer of a 2-phase liquid, exhibits a color indicative of the pH of the oil and further indicative of the concentration of the anti-corrosive additive existing within the used oil. Comparison of this color with color values obtained from practicing the method of the present invention on unused lubricating oil samples provides information indicative of the change of pH of the representative sample of freshly removed lubricating oil, hence the change of pH of the oil then in use in the machines or engines. For example, the representative comparison value may be obtained in pH units.

The method of making the above-referenced comparisons is not critical to the present invention. Accordingly, such comparisons may be made by standard spectrophotometric methods or by visually comparing the color of the reacted oil sample with the color generated by practicing the present invention on the unused oil. Further, the comparison may also be made by visually comparing the oil-generated color with a color chart which reproduces the color generated by the unused oil.

By testing samples of freshly removed oil at different times, one is thus able to derive data indicative of any change in pH, hence concentration of anti-corrosive additive existing within the used oil. For example, a change in the pH value towards a value of approximately pH 2 represents an increase of acidic corrosive materials in the lubricating oil and a corresponding decrease in the concentration of the active anti-corrosive additive in the lubricating oil. A change in pH value toward a value of pH 10 represents an increase in active anti-corrosive additive concentration and/or an increase in basic contaminant material in the lubricating oil. Additionally, an increase in pH towards 10 may also indicate further contamination of the lubricating oil. For example, in certain industries such as the petrochemical industry, machines or engines are used in corrosive atmospheres. In these atmospheres, gaseous materials such as, for example, ammonia may be absorbed by the oil. In this event, the gaseous materials may react with other contaminants in the oil or with water to produce basic compounds which effect the pH of the lubricating oil.

In order to further standardize the obtained analytical results, it is preferred that the method disclosed herein be first performed on an unused lubricating oil of the same type and grade that is subsequently to be placed in an operating machine or engine. The color which is obtained from such unused lubricating oil testing may be further compared to the colors generated by practicing the present invention on standardized acidic and/or basic solutions. It is also preferred that one or more analyses be performed on freshly removed oil after the lubricating oil has been placed within the operating environment of the machine or engine.

Whenever the subsequent analysis establishes that the pH level has exceeded the norm for the specific oil in use, the concentration of the anti-corrosive additive has decreased sufficiently to warrant replacement of the oil.

As a further example, but without limitation, the method disclosed herein may be performed as follows:

Step 1. Place 4.5 ml of the selected solvent-reagent into a sample test tube capable of being capped;

Step 2. Place 4.5 ml of freshly removed oil in the sample test tube used in step 1, and cap the tube;

Step 3. Shake the solution resulting from step 2 thoroughly for approximately 15 seconds until the solution is well mixed;

Step 4. Place the tube in a vertical position and allow to remain unattended for approximately 5 minutes or until the sample and solvent layers achieve separate phases;

Step 5. Compare the color in the lower layer of the liquid phase to the color of the same phase obtained by performing steps 1 through 4 on a representative sample of unused oil to obtain an comparison value indicative of the pH of the freshly removed oil and further indicative of the decrease in concentration of the anti-corrosive additive.

Furthermore, distilled water is an appropriate solvent to use in the practice of this method. The solvent dissolves organic acids, mineral acids and bases, and acidic and/or basic salts that may exist in the lubricating oil sample. Additionally, colorimetric reagents such as, for example, a mixture of thymol blue and methyl orange are useful. Such mixture permits the determination of the pH of the oil sample from a pH of approximately 2 to a pH of about 10 by providing a reagent which changes color depending upon the pH of the oil. Table 2 provides an example of a typical solvent-reagent system together with the absorbance for varying pH values.

TABLE 2.

Solvent-468 ml distilled water
Reagent-35 ml thymol blue;
7 ml methyl orange

| pH | ABSORBANCE (m$\mu$) |
|---|---|
| 2 | 490–500 (red) |
| 4 | 480–490 (orange) |
| 6 | 435–480 (yellow) |
| 9 | 560–595 (violet) |

Representative absorbance values for varying pH values of a typical solvent-reagent system for pH determination.

EXAMPLES

In order to establish the efficacy of the invention disclosed herein a series of experiments are performed on oil samples removed from an operational engine. Table 3 provides the parameters of the operational environment of this engine and certain additional chemical data.

TABLE 3.

Oil sample data and chemical analysis of oil removed from an oil pumping station at Alden, Kansas (Michigan-Wisconsin Pipeline).

| SAMPLE DATA | | SAMPLE ANALYSIS | |
|---|---|---|---|
| Engine | # 309-IR | Viscosity @ 100° F.,SUS | 752 |
| Data Sampled | 7-21-77 | Viscosity @ 210° F.,SUS | 78.2 |
| Oil | HDG-30 | Viscosity Increment @ 210° F., % | 16.0 |
| Oil Hours | 2926 | TAN[1], Mg KOH/g | 7.7 |

1. Total Acid Number; a TAN value of 7.7 is approximately equal to a pH of 3.5 to 4.0.

EXAMPLES 1—IRON CONTAMINANT

A solvent is prepared by dissolving 15.0 g hydroxylamine hydrochloride in 500 ml $H_2O$ (distilled). To this solvent is added 5.0 g of the reagent $\alpha,\alpha,'$ dipyridil.

Approximately 4.5 ml of freshly removed oil is placed in a test tube containing approximately 4.5 ml of the solvent-reagent solution. The test tube is capped and vigorously shaken for about 15 seconds and then permitted to stand in a vertical position for about 90 minutes. The mixture, upon standing, separates into two layers or phases with the solvent-reagent phase as the lower layer and the oil phase as the upper layer. The lower layer displays a color, with an absorbance measured in the range of approximately 520–522 m$\mu$. Comparison of the color intensity of this sample with that obtained from performing this procedure on an iron organo-metallic standard containing a known amount of iron indicates the freshly removed oil sample contains approximately 60 parts per million iron.

Table 4 presents data obtained from an emission spectrograph analysis performed on a sample of the freshly removed oil used in this example. Reference to this Table indicates that the sample contains approximately 70 ppm iron as a contaminant, thus establishing the reliability of the procedure disclosed herein.

TABLE 4.

Emission spectrograph data obtained from the oil sample of Table 3.

| METAL | CONCENTRATION, ppm |
|---|---|
| Iron | 70 |
| Copper | 178* (50) |
| Chromium | 5 |
| Tin | 9 |

*This value was believed to be erroneous and a second emission spectrograph was run. The results of this second run are presented parenthetically.

EXAMPLE 2—COPPER CONTAMINANT

A solvent is prepared by dissolving 15.0 g hydroxylamine hydrochloride in 500 ml $H_2O$ (distilled). To this solvent is added 0.5 g of the reagent bathocuproine disulfonic acid disodium salt.

Approximately 4.5 ml of freshly removed oil is placed in a test tube containing approximately 4.5 ml of the solvent-reagent solution. The test tube is capped and vigorously shaken for about 15 seconds and then permitted to stand in a vertical position for about 90 minutes. The mixture, upon standing, separates into two layers or phases with the solvent-reagent phase as the lower layer and the oil phase as the upper layer. The lower layer displays a color, with an absorbance measured in the range of approximately 476–479 m$\mu$. Comparison of the color intensity of this sample with that obtained from performing this procedure on a copper organo-metallic standard containing a known amount of copper indicates the freshly removed oil sample contains approximately 70 parts per million iron.

Table 4 indicates that initial emission spectrographs establishes the sample contains approximately 178 ppm copper as a contaminant, however, a second emission spectrograph analysis shows the initial value to be erroneous. The second spectrograph indicates the Cu concentration to be in the range of 50 ppm.

EXAMPLE 3—CHROMIUM CONTAMINANT

A solvent is prepared by dissolving 5.0 ml. chromotropic acid disodium salt in 495 ml $H_2O$ (distilled). To this solvent is added 25.0 g of the reagent 85% phosphoric acid.

Approximately 4.5 ml of freshly removed oil is placed in a test tube containing approximately 4.5 ml of the solvent-reagent solution. The test tube is capped and vigorously shaken for about 15 seconds and then permitted to stand in a vertical position for about 90 minutes. The mixture, upon standing, separates into two layers or phases with the solvent-reagent phase as the lower layer and the oil phase as the upper layer. The lower layer displays a color, with an absorbance measured in the range of approximately 542–540 m$\mu$. Comparison of the color intensity of this sample with that obtained from performing this procedure on a chromium organometallic standard containing a known amount of chromium indicates the freshly removed oil sample contains less than 10 parts per million chromium.

Reference to Table 4 indicates the oil contains approximately 5 ppm chromium.

EXAMPLE 4—TIN CONTAMINANT

A solvent-reagent solution is prepared by dissolving 12.5 g ammonium molybdate in 500 ml $H_2O$ (distilled).

Approximately 4.5 ml of freshly removed oil is placed in a test tube containing approximately 4.5 ml of the solvent-reagent solution. The test tube is capped and vigorously shaken for about 15 seconds and then permitted to stand in a vertical position for about 5 minutes. The mixture, upon standing, separates into two layers or phases with the solvent-reagent phase as the lower layer and the oil phase as the upper layer. The lower layer displays a color, with an absorbance measured in the range of approximately 715–840 m$\mu$. Comparison of the color intensity of this sample with that obtained from performing this procedure on a tin organometallic standard containing a known amount of tin indicates the freshly removed oil sample contains less than 10 parts per million iron.

Reference to Table 4 shows the oil contains approximately 9 ppm tin. Comparison of the spectrograph result with the result of the procedure disclosed herein establishes the efficacy of the present invention.

EXAMPLE 5—ACTIVE ANTI-CORROSIVE ADDITIVE

A solvent-reagent solution is prepared by dissolving 7 ml of methyl orange and 35 ml of thymol blue in 468 ml of distilled water. Approximately 4.5 ml of freshly removed oil is placed in a test tube containing about 4.5 ml of the solvent-reagent solution. The tube is capped and vigorously shaken for about 15 seconds and then permitted to stand in a vertical position for about 5 minutes. The mixture, upon standing, separates into two layers or phases with the solvent-reagent phase as the lower layer and the oil phase as the upper layer. The lower layer displays a color, with an absorbance measured in the range of approximately 482 m$\mu$. Comparison of the color intensity of this sample with that obtained from performing this procedure on an active anti-corrosive additive standard with a known pH value indicates the freshly removed oil sample has a pH value of about 5.

THE ANALYSIS KIT

The method of the present invention may be easily practiced by a person who has not previously received training normally associated with a chemist or highly skilled technician. To this end, the invention also provides a lubricating oil analysis kit 10 as shown in FIG. 1, with the components of the kit being preselected by the manufacturer to permit analysis for one or more contaminant materials. Preferably, the kit of the present invention contains at least one receptacle 12 adapted to be closed on one end 14 thereof and of sufficient volume to hold approximately 5 ml of solvent-reagent and approximately 5 ml of lubricating oil. Preferably, each receptacle, prior to receipt by the user, contains a predetermined volume of a preselected solvent-reagent solution adapted for analysis of a specific contaminant. For example, the receptacle may be a 30 ml volume test tube externally threaded on the open end thereof and adapted to receive a threaded cap 16 thereupon. Further, it is preferred that the solvent-reagent solution be pre-mixed by the manufacturer thereof, with the solution being stored in a capped receptacle during shipment. Also included in the kit is a dispensing device 18 for measuring a known volume of freshly removed oil and for adding the measured volume to the solvent-reagent containing receptacle. Such apparatus may, for example, be a graduated buret or an eye-dropper-type device of known voume. Alternatively, the above-referenced receptacle may be graduated as indicated by line 20 such that addition of the oil to the receptacle may be carried out until a known amount of lubricating oil is added thereto. It is preferred to assure that the dispensing device does not become contaminated during shipment of the kit, and prior to use thereof. Accordingly, the device may be sealed, such as in a plasticized wrapper or in an empty receptacle such as that used to contain the solvent-reagent solution.

In using the kit of the present invention, the user first obtains a representative sample of freshly removed oil. Thereafter, a volume of the oil is obtained by withdrawing the volume with the dispensing device. The volume is then placed in the receptacle containing the solvent-reagent solution until a known volume of oil has been added. Analysis thereafter proceeds as previously described.

In order to enable the user to accurately determine the concentration of contaminant materials existing in the freshly removed oil sample, and to obviate the need for the user to establish standardized color intensities by performing the method of the invention on organo-metallic and/or pH standards, the kit is provided with a color chart 22 that accurately reproduces the color intensities for varying concentrations of the several metallic, acidic, and basic contaminants. For example, for each specific metallic contaminant analyzable by the present invention, the color chart may provide representative color intensities for one or more concentration levels, such as 10, 50 and 100 parts per million. Thus, after the color is generated for each metal contaminant tested, the intensity is compared to the appropriate color chart intensity level to determine the approximate level of contaminant concentration. Determination of the pH of the oil sample proceeds in the same fashion.

While the invention has been described with reference to preferred embodiments, alternatives thereto and certain examples, it should be realized that one skilled in the art may make modifications or changes to the invention while still falling within the scope and spirit of the disclosure. Accordingly, all such modifications or changes should be deemed to be a part hereof. For example, in the various examples provided herein one volume of solvent-reagent solution is mixed with an approximately equal volume of freshly removed oil sample. One skilled in the art will readily appreciate that this ratio is variable depending on the solvent and reagent concentrations and, therefore, the examples are not meant to be limiting in any manner.

What is claimed is:

1. A lubricating oil analysis kit to analyze for a metallic contaminant that may be present in lubricating oil comprising:
    at least one receptacle adapted to be opened and closed on one end thereof and containing therein an aqueous solvent and a reagent both present in predetermined concentration, said aqueous solvent effective to dissolve the preselected contaminant existing within the oil but not effective to dissolve the oil so as to form an oil phase and an aqueous phase containing the dissolved preselected contaminant and said reagent capable of reacting with the dissolved contaminant and thereby causing a color to be generated in the aqueous phase;
    a dispensing device adapted to dispense a volume of lubricating oil into said receptacle, the capacity of said receptacle being at least equal to the sum of the volumes of said oil phase and said aqueous phase;
    a color intensity chart adapted for use in comparing color intensities generated when said aqueous solvent and said reagent are mixed with lubricating oil to determine the concentration of the preselected contaminant which may be existing within said oil.

2. The kit of claim 1, wherein said reagent is chosen from the group consisting of $\alpha,\alpha'$ dipyridil; bathocuproine disulfonic acid disodium salt; chromotrophic acid disodium salt; ammonium molybdate; and dimethylglyoxime disodium salt and ammonium tartrate.

3. The kit of claim 1 wherein said solvent is chosen from the group consisting of water, an aqueous solution of phosphoric acid, and an aqueous solution of hydroxylamine hydrochloride.

4. The kit of claim 3, wherein said reagent is chosen from the group consisting of $\alpha,\alpha'$ dipyridil; bathocuproine disulfonic acid disodium salt; chromotrophic acid disodium salt; ammonium molybdate; and dimethylglyoxime disodium salt and ammonium tartarate.

5. A kit for analyzing for a contaminant which may be present in an oil, comprising:
- a receptacle adapted to be opened and closed on one end thereof;
- a volume of an aqueous liquid which is substantially immiscible with said oil, said aqueous liquid being in said receptacle;
- means for adding a volume of said oil to said receptacle into contact with said aqueous liquid to form an oil phase and an aqueous phase distinct from one another, the capacity of said receptacle being at least equal to the sum of the volumes of said aqueous phase and said oil phase;
- a reagent in said aqueous liquid which reacts with said contaminant in said aqueous phase on extraction thereof into said aqueous phase to produce a color change in said aqueous phase; and
- means for comparing the color of said aqueous phase after vigorous mixing thereof with said oil and substantially full separation of said phases from one another, said color having been generated by the reaction of said reagent with said contaminant, with the color of at least one aqueous phase standard having said reagent therein and which has a known amount of the same contaminant.

6. A kit as in claim 5, wherein said aqueous liquid is water, an aqueous solution of phosphoric acid, or an aqueous solution of hydroxylamine hydrochloride.

7. An on-site method for determining the need for replacement of oil due to the build up of metallic contaminant material therein, which comprises the steps of:
- removing a sample of oil, the oil being suspected of having a build up of metallic corrosive material therein, to provide a sample of oil;
- vigorously mixing a known volume of said sample of oil in a known volume of an aqueous solvent which extracts metal and/or metal oxides existing within the oil from the oil into the aqueous solvent to form an aqueous phase comprising an aqueous solvent solution of said metallic contaminant material, said aqueous solvent solution including a reagent capable of reacting with the metal and/or metal oxide in the aqueous phase to generate a color in the aqueous phase indicative of the presence and concentration of said metallic contaminant, said aqueous solvent not being effective to dissolve the oil whereby distinct oil and aqueous phases are intimately mixed together;
- allowing the oil phase to separate from the aqueous phase; and
- comparing the color as generated in the aqueous phase by the reaction of said reagent with said metal and/or metal oxide to a standard color to determine the concentration of said metallic contaminant material.

8. The method of claim 7, wherein said aqueous solvent is chosen from the group consisting of water, an aqueous solution of phosphoric acid and an aqueous solution of hydroxylamine hydrochloride.

9. The method of claim 7 wherein said metallic contaminant material is chosen from the group consisting of iron, copper, chromium, tin and nickel.

10. A method as in claim 7, wherein said vigorous mixing is for a selected standard period of time.

11. The method of claim 7, wherein said reagent is chosen from the group consisting of $\alpha,\alpha'$ dipyridil, bathocuproine disulfonic acid disodium salt, chromotrophic acid disodium salt and ammonium molybdate.

12. The method of claim 11 wherein said metallic contaminant material is chosen from the group consisting of iron, copper, chromium, tin and nickel.

* * * * *